(12) United States Patent
Studer (10) Patent No.: US 7,217,394 B2
(45) Date of Patent: May 15, 2007

(54) APPARATUS FOR HANDLING BIOPSY SPECIMENS, AND METHOD FOR USING IT

(75) Inventor: Daniel Studer, Dotzigen (CH)

(73) Assignee: Leica Mikrosysteme GmbH, Vienna (AT)

( * ) Notice: Subject to any disclaimer, the term of this patent is extended or adjusted under 35 U.S.C. 154(b) by 630 days.

(21) Appl. No.: 10/366,567

(22) Filed: Feb. 14, 2003

(65) Prior Publication Data

US 2003/0198574 A1    Oct. 23, 2003

(30) Foreign Application Priority Data

Feb. 14, 2002    (CH) .................................... 0257/02

(51) Int. Cl.
B01L 3/00    (2006.01)

(52) U.S. Cl. ............................. 422/99; 422/64; 422/65; 422/100; 422/101; 436/43; 436/180; 435/243

(58) Field of Classification Search .......... 422/99–101, 422/64, 65; 435/283.1, 243; 436/180, 43
See application file for complete search history.

(56) References Cited

OTHER PUBLICATIONS

E. Shimoni et al., "On optimizing high-pressure freezing: from heat transfer theory to a new microbiopsy device", Journal of Microscopy, vol. 192, Pt 3, Dec. 1998, pp. 236-247.
D. Studer et al., "Vitrification of articular cartilage by high-pressure freezing", Journal of Microscopy, vol. 179, Pt 3, Sep. 1995, pp. 321-332.
H. Hohenberg et al., "High-pressure freezing of tissue obtained by fine-needle biopsy", Journal of Microscopy, vol. 183, Pt 2, Aug. 1996, pp. 133-139.
Leica Microsystems GmbH, "Leica EM Pact—High Pressure Freezer", Product Information, No. 16 50 02, Dec. 2000.

*Primary Examiner*—Jill Warden
*Assistant Examiner*—Jyoti Nagpaul
(74) *Attorney, Agent, or Firm*—Foley & Lardner LLP (57) ABSTRACT

An apparatus for handling biopsy specimens comprises a transfer part, a slide displaceable in a groove of said transfer part, preparation plates for the reception of biopsy specimens, and a shifter part that serves to introduce the biopsy specimens into the preparation plates. The empty preparation plates are positioned at a predetermined point in the groove of the transfer part, and the shifter part is placed onto the transfer part above the preparation plates. The biopsy specimens are then introduced into the specimen well of a preparation plate by manually actuated instruments or by means of a stream of fluid. The filled preparation plate is displaced back in the groove of the transfer part using the slide, and is transferred into a specimen holder prepared for it.

21 Claims, 10 Drawing Sheets

APPARATUS FOR HANDLING BIOPSY SPECIMENS, AND METHOD FOR USING IT

CROSS REFERENCE TO RELATED APPLICATIONS

This application claims priority of the Swiss patent application 0257/02 which is incorporated by reference herein.

FIELD OF THE INVENTION

The invention refers to an apparatus for handling biopsy specimens, and to a method for using it.

BACKGROUND OF THE INVENTION

Modem electron microscopy of biological specimens is more and more frequently examining specimens that have been immobilized by freezing (cryofixation). Freezing must be performed in such a way that the specimens vitrify, i.e. so that upon cooling, no ice (which would segregate the specimen) can form. "Segregation" is the separation of the specimen into pure water (ice crystals) and concentrated dissolved substances between the branches of the ice crystals. In vitrification, water is immobilized in its liquid configuration. In other words, all the constituents of the biological specimen are not displaced during immobilization, and thus represent a "snapshot" of the living material at the moment it was fixed. Vitrification in a biological system is a rapid process: a freezing rate of several 100,000 K/s is normally necessary. For physical reasons, such high freezing rates can be achieved only in very thin specimens (thickness <20 µm). The critical freezing rate necessary for vitrification can be reduced by a factor of 100 if the specimen is frozen at a pressure of approximately 2000 bar. In so-called high-pressure freezing (Studer et al., Journal of Microscopy 179 (1995), 321–332), biological specimens approx. 200 µm thick are vitrified. Production of a 200 µm-thick specimen with a diameter of 1.2 to 3 mm is difficult. The advantages of high-pressure freezing are reduced if a great deal of time is spent preparing the biological specimens, e.g. a piece of tissue, for freezing. Individual attempts at rapid preparation of very small tissue pieces have been described by various authors (H. Hohenberg et al., Journal of Microscopy 183 (1996), 133–139; E. Shimoni et al., Journal of Microscopy 192 (1998), 236–247). Shimoni et al. fired small metal capillaries (gold tubules with an inside diameter of 200 µm) into the tissue; locating these capillaries in the tissue is time-consuming, however, and the frozen specimens are difficult to process. Hohenberg et al. (1996) took tissue samples 0.2–0.25×0.4×4–8 mm in size from experimental animals, using commercially available microbiopsy needles adapted for that particular purpose.

Commercially obtainable apparatuses for taking microbiopsy samples from living tissue have a spring mechanism (gun) that receives a needle (for example, Pro-Mag™, Manan Medical Products, Inc., Northbrook, Ill. 60062, USA). This biopsy needle in turn comprises a solid lance (diameter 0.6–3 mm) having an opening, 8–16 mm long and 0.3–2 mm deep, for receiving the biopsy material (Hohenberg op. cit. FIG. 1-D, pp. 134–35). This lance is pointed at one end, and has a holding device at the other end. This lance is in turn surrounded by a thin-walled hollow needle whose inside diameter corresponds to the outside diameter of the lance, so that the lance and hollow needle are displaceable with respect to one another. The hollow needle has a cutting edge at one end and a holding device at the other.

The hollow needle, and the lance inserted in it, are secured with the holding devices in the gun, so that the mechanism for removal of the biopsy material is as follows: First the needle, inserted into the gun, is introduced into the tissue, so that the hollow needle allows only the tip of the lance to protrude. Then the spring mechanism is released. As a result, firstly the lance is advanced farther into the tissue so that the opening is no longer enclosed by the hollow needle. The tissue enters the opening, and at the next instant the hollow needle with the cutting edge is in turn slid over the opening by the spring mechanism. The piece of tissue present in the opening is thereby cut off. The hollow needle, together with the lance, is then pulled back out of the tissue, and the outer hollow needle is once again slid back with respect to the lance so that the cut-out specimen becomes accessible.

Biopsy specimens obtained in this fashion have, for example, the following dimensions: 200 to 250 µm high, 400 µm wide, and 4 to 8 mm long (Hohenberg, op. cit., p. 135). These specimens are manually reduced in size using suitable cutting tools (razor blades, scalpels, or the like), cut to the correct size, and transferred with forceps or other suitable instruments into the specimen plates of appropriate high-pressure freezing units.

This manual preparation of biopsy specimens for high-pressure freezing exhibits, however, a number of serious disadvantages which reveal this method to be unsuitable for larger quantities of specimens and especially for routine operation. The elapsed time between excision of the biopsy material and the beginning of the freezing operation has been quoted as approx. 40 seconds (Hohenberg op. cit. p. 135); experience has shown, however, that this is a very optimistic time scale. This elapsed time is obviously too great, particularly in cases in which "snapshots" need to be prepared of cells whose ultrastructure changes rapidly, for example muscle cells. A further disadvantage of manual manipulation of biopsy specimens is the fact that the gelatinous consistency and small dimensions of the tissue specimens considerably complicate reliable manual manipulation thereof, so that the reproducibility of the results is low and the reject rate is considerable. This in turn not only is undesirable for general cost reasons, but also is unacceptable especially in situations in which consideration must be given to the patient/examination subject or experimental animal, and excision of biopsy material therefore cannot be repeated an unlimited number of times, for example in the case of removal of specimens from a living myocardium. Lastly, the most important disadvantage of manual manipulation of biopsy specimens is the fact that this manipulation is so difficult to perform that, as indicated by experience, only a small percentage of the technical personnel of an institution are at all capable, even after extended training, of producing perfect or at least satisfactory specimens. The results of manual preparation are therefore poorly reproducible, and the user of commercial equipment must resort to employing, for preparation, persons who by fortunate accident possess manual and motor skills far above the average.

SUMMARY OF THE INVENTION

It was accordingly the object of the present invention greatly to increase the speed of the preparation operation (time requirement between excision and onset of freezing less than 30 seconds), and thereby to improve the quality of the snapshots of the specimens being examined. A further object of the invention was to improve the reliability and reproducibility of the preparation process as compared to manual preparation. Lastly, the further object presented was to decrease the manual and motor demands on implementing personnel, i.e. to facilitate working procedures for preparation and thereby to give even technical personnel of average training and skill the capability of producing perfect specimens.

The apparatus according to the present invention makes it possible greatly to increase the speed with which biopsy material is prepared: the time for a specimen removal operation, measured from insertion of the microbiopsy needle to completion of the initial freezing operation, is a maximum of 30 seconds. The reliability and reproducibility of preparation results has been considerably increased, and rejects have been practically entirely eliminated. Working procedures during preparation have been simplified, with the apparatus according to the present invention, in such a way that preparation can be reliably performed by technical personnel with average training and average manual skills.

BRIEF DESCRIPTION OF THE DRAWINGS

Preferred embodiments of the apparatus and its use will be presented by way of example below with reference to the drawings, the invention not being limited to these particular embodiments that are presented. The following components of the apparatus are depicted in the drawings, in perspective in each case:

FIGS. 7 through 11 depict, by way of example, the various steps of the method for handling biopsy specimens using the method according to the present invention. In these Figures:

DETAILED DESCRIPTION OF THE INVENTION

The apparatus according to the present invention includes biopsy needles, only partially depicted in the FIGS., which have an opening for receiving the biopsy specimen that is substantially reduced in size compared to commercially obtainable products (for example, Pro-Mag™, Manan Medical Products, Inc., Northbrook, Ill. 60062, USA). The opening is, for example, 0.2–0.3 mm deep and only 1.2 mm long; this yields a volume for the resulting biopsies that corresponds to the volume of the specimen well of the preparation plate. The needle is permanently secured in the biopsy gun, so that the inner lance, with the opening for the biopsy material, is immovable with respect to the biopsy gun.

Figure 1A:
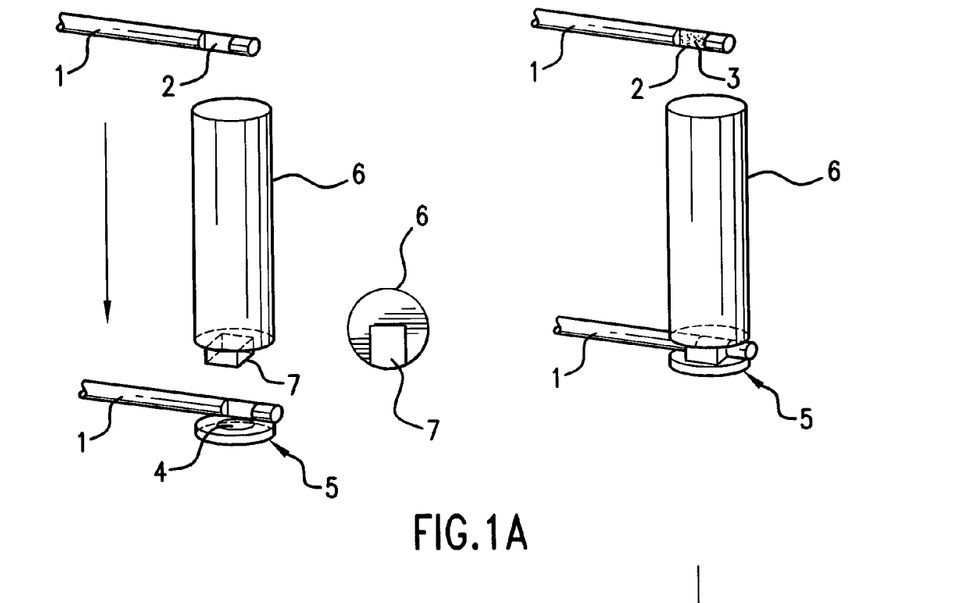
FIGS. 1a and 1b show the two principles of biopsy transfer from the opening in the biopsy needle to the specimen well of the preparation plate.

FIG. 1a shows two embodiments for transferring biopsy specimens using the apparatus according to the present invention. A biopsy specimen 3 is introduced into the empty opening 2 of a biopsy needle 1. The needle filled with this biopsy specimen is centered on specimen well 4 of a preparation plate 5. By advancing cylindrical shaped part 6 with its accurately fitting shaped tip 7, the biopsy specimen is then transferred out of opening 2 into specimen well 4.

Figure 1B:
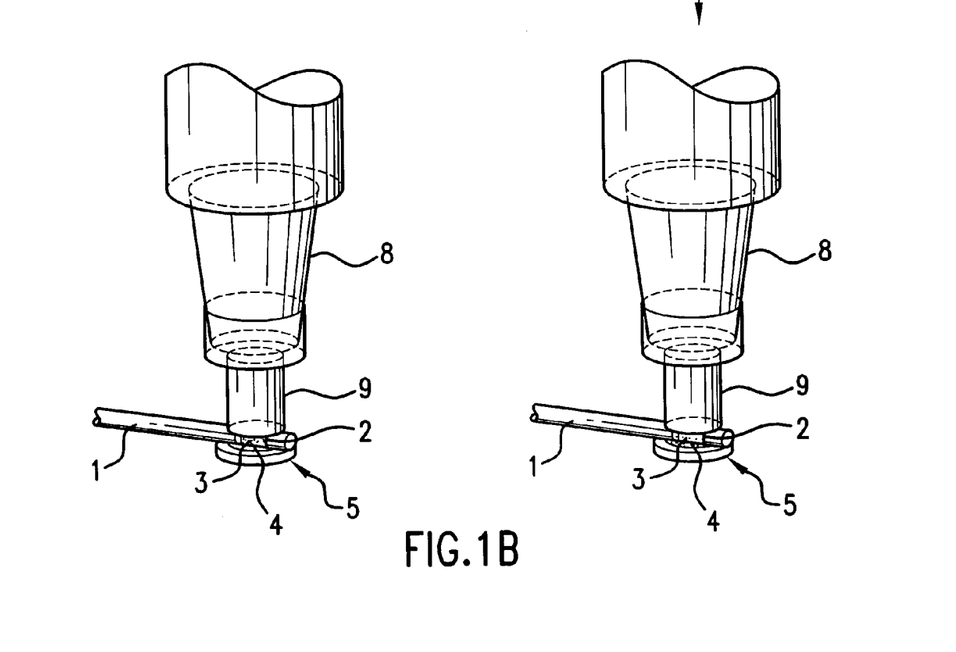

FIG. 1b shows the manner in which a biopsy 3 can be transferred from opening 2 of biopsy needle 1 into specimen well 4 by means of a stream of fluid. A transition part 9 that connects syringe 8 and opening 2 is mounted onto a commercially obtainable injection syringe 8. This transition part 9 has at the upper end a cavity for reception of injection syringe 8; at its lower end it is shaped in such a way that its cross section corresponds to the shape of opening 2 of biopsy needle 1. By displacement of the piston of injection syringe 8, the biopsy specimen is flushed by means of a stream of fluid (buffer solution, 1-hexadecene, etc.) into specimen well 4 of a preparation plate 5.

Figure 2A:
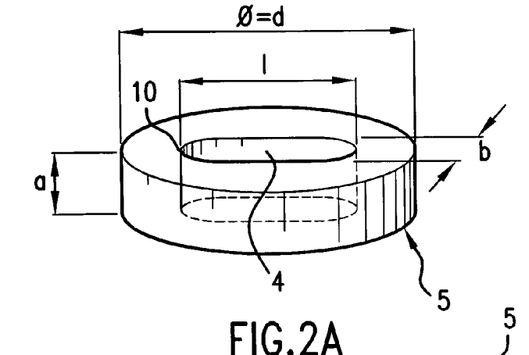
FIGS. 2a through 2f show various embodiments of preparation plates.
Figure 2B:
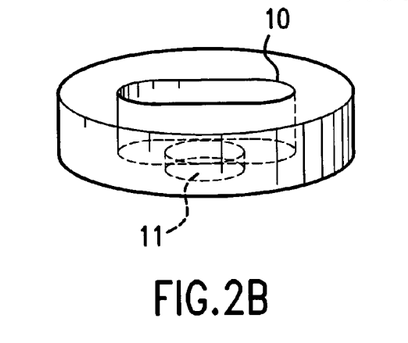
Figure 2C:
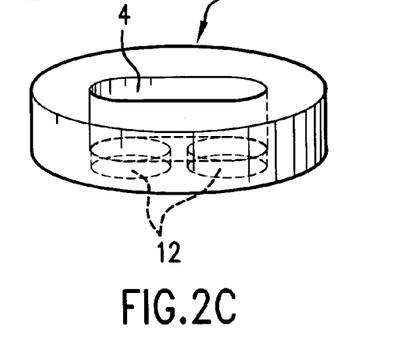
Figure 2D:
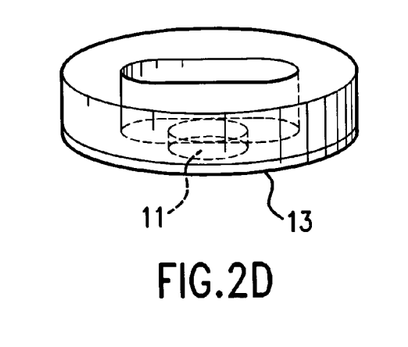
Figure 2E:
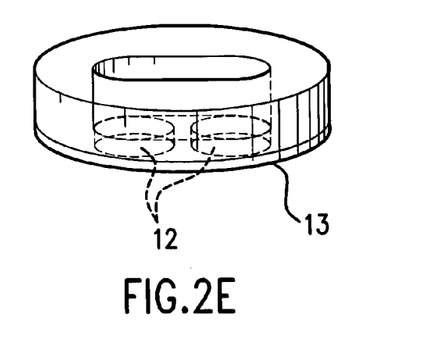
Figure 2F:
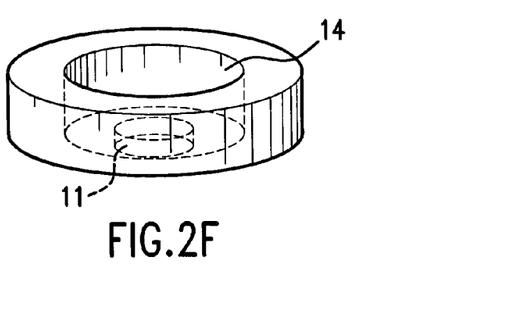

Preparation plates 5, depicted in FIGS. 2a through 2f at enlarged size compared to the other Figures, are made of a material with good thermal conductivity—for example a metal, preferably from the series copper, brass, titanium, aluminum—and have a specimen well 4 that is embodied as a slot (in FIG. 2f as a circular depression). Plates made of comparatively soft copper sheet, as used for example in the building trades, have proven particularly successful for this purpose. Other geometrical shapes are usable as an alternative to the circular shape of these preparation plates depicted in FIG. 2. In that case the shape of recess 22 of slide 21 (FIG. 4) must be adapted accordingly. If shapes other than circles are used for preparation plates 5, this offers the additional advantage that the geometrical orientation of preparation plate 5 and of specimen well 4 can be predetermined in accordance with recess 22 of slide 21. Slot thickness b of specimen plate 5 emerges as a critical factor: it should not exceed 0.3 mm. If a >2b, then b should not exceed 0.2 mm. For production-engineering reasons, specimen well 4 advantageously ends in a semicircle 10, but other geometrical shapes are also permissible. The physical, thermal, and pressure-related properties of the preparation plates, and of the biological specimen being frozen, define the range of advisable dimensions. For the preparation plates proposed, these are a=0.3–5 mm, l=0.3–5 mm, and, as described above, b=0.2–0.3 mm. Diameter d must be at least l+0.6 mm, and should be no more than l+2 mm. In an exemplary embodiment, the preparation plates that are used have, for example, the following dimensions: a=0.6 mm, b=0.3 mm, l=1.2 mm, d=3 mm. The following morphological variants have proven useful:

FIG. 2a: Metal disk having specimen well 4. This shape offers the advantage that it can be manufactured easily and cheaply, but has the disadvantage that depending on the consistency of the specimen, the latter can be lost in some circumstances during transfer from the shifter part into the specimen holder.

FIGS. 2b and 2c: Metal disks having a slot-shaped depression that extends only 0.05–0.1 mm onto the opposite side. The depression is cut through at center 11 (FIG. 2c) or at both ends 12 (FIG. 2c). This variant offers the advantage that the specimens cannot be lost during transfer.

FIGS. 2d and 2e: Metal disks having the same geometry as FIGS. 2b and 2c, but fabricated from two permanently assembled parts. These variants are manufactured by fitting a plate according to FIG. 2a to a metal foil 13 having corresponding holes 11 and 12, for example by adhesive bonding with a suitable adhesive.

FIG. 2f: This plate corresponds approximately to the plate of FIG. 2b. It contains a circular depression 14 rather than a slot-shaped one. This embodiment is not as good as plates 2a through 2e as regards freezing, but in terms of manufacture it is by far the most economical preparation plate variant.

Figure 3:
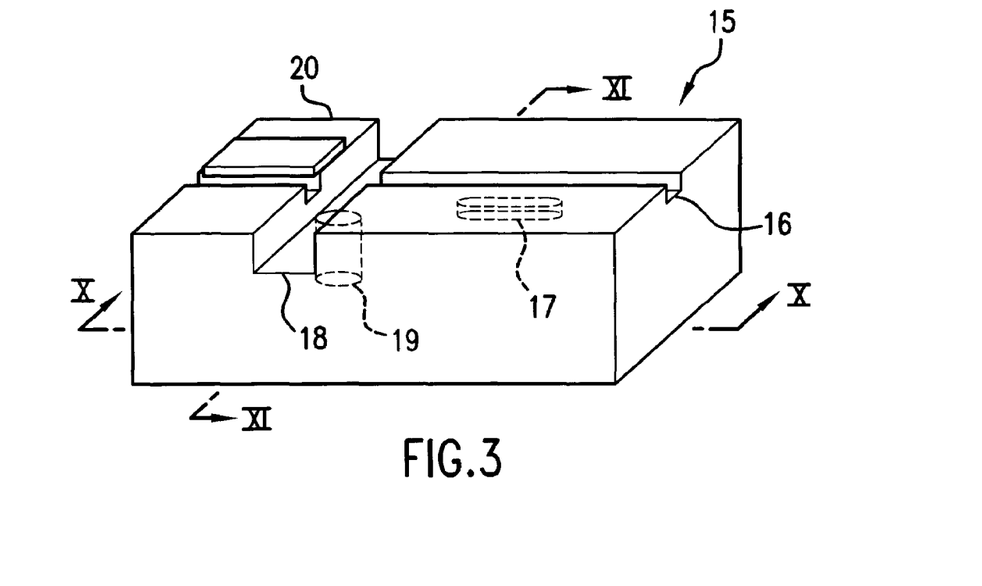
FIG. 3 shows a transfer part.
Figure 5:
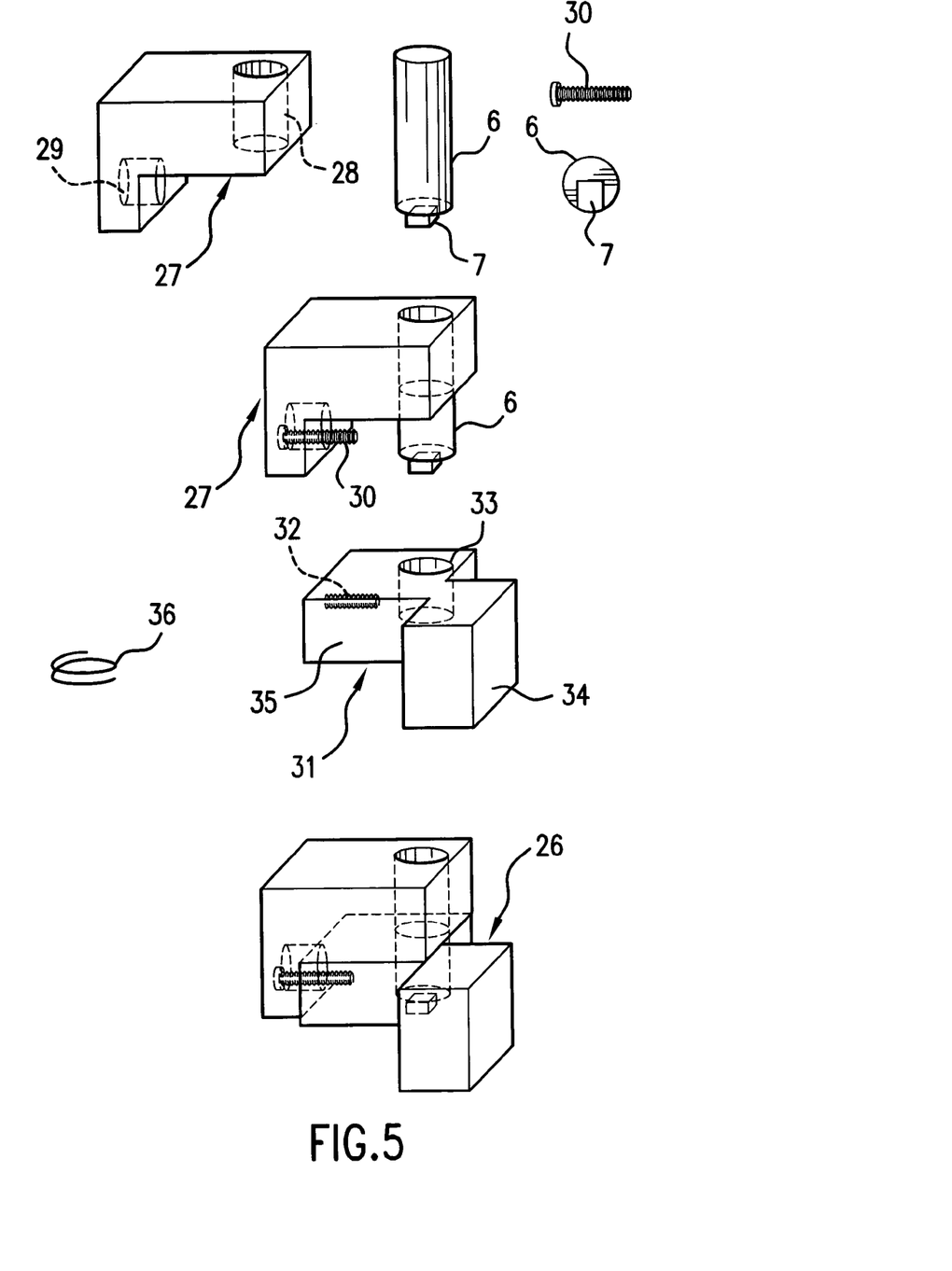
FIGS. 5 and 6 show two different embodiments of shifter parts, one of which is made up of several parts.

The embodiment of a transfer part depicted by way of example in FIG. 3 comprises a parallelepipedal shaped part 15 made of a material having a smooth surface and chemical resistance to the fluids used in freezing technology, for example 1-hexadecene, buffer solutions, carbohydrate solutions, etc. Metal alloys, in particular aluminum alloys, or plastics, for example POM, have proven successful as appropriate materials for this transfer part. This shaped part 15 has, on its upward-facing surface, a groove 16 extending through the entire length. Recessed into this groove is a second groove 17, of defined length and position, for reception of a slide 21 and positioning thereof in groove 16. Extending perpendicular to groove 16 is a deeper groove 18 that serves for reception and accurate positioning of a specimen holder 39 by means of hollow-cylindrical opening 19, and for exact positioning of a shifter part 26 (FIG. 5). The shorter part of groove 16 cut off by groove 18 is overlapped by a plate 20 permanently mounted on the upper side of shaped part 15, in such a way that a defined cavity is created which makes possible accurate positioning of an introduced biopsy needle 1.

The purpose of this transfer part 15 is to make preparation plates 5 available at the correct point for reception of biopsy specimens; then to receive the specimens in said preparation plates 5; and to transfer preparation plates 5, filled with the specimens, into suitable specimen holders.

Figure 4:
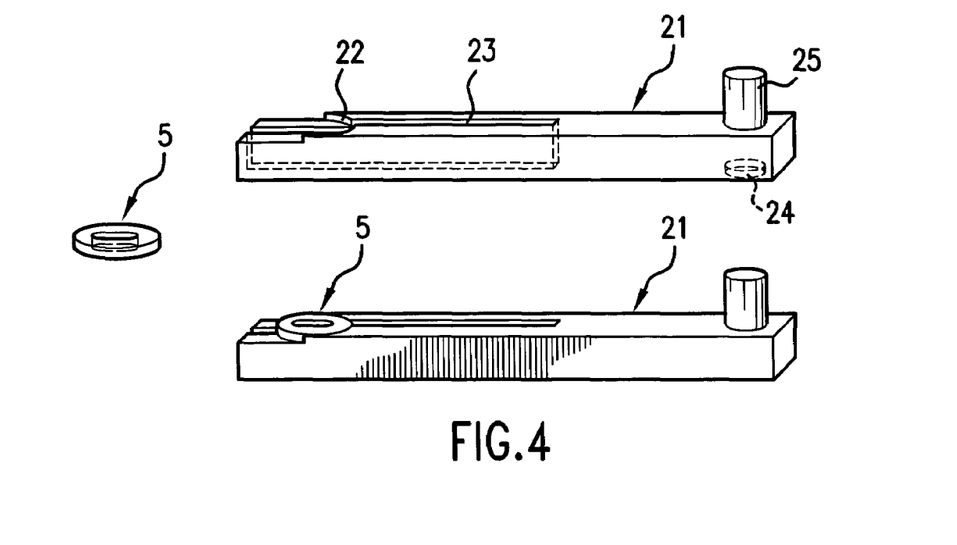
FIG. 4 shows a slide with an inserted preparation plate, at an enlarged scale.

Slide 21 depicted at enlarged size in FIG. 4 comprises a parallelepipedal strip of a suitable material, preferably the same material as shaped part 15 (for example, POM). It is dimensioned in such a way that it can easily be displaced manually in longitudinal groove 16 of shaped part 15. This slide 21 has at one end a cut-out circular arc 22 of approx. 220°, which corresponds in its dimensions to the dimensions of a preparation plate 5 and can receive the latter for displacement within groove 16. This recess 22 can also be of non-circular configuration, corresponding to the geometrical shape of preparation plate 5 that is used. The orientation of preparation plate 5 and of specimen well 4 in slide 21 can thereby be predetermined according to the user's wishes. This slide 21 furthermore has a vertical slot 23, extending in the longitudinal axis, which enables biopsy specimen 3, transferred into a preparation plate 5, to be introduced into a suitable specimen holder 39. Peg 24 on the underside of slide 21 serves to position slide 21 in groove 17. Its end directed toward groove 18 defines the position for the transfer of biopsy specimen 3 from biopsy needle 1 into preparation plate 5; the other end defines the position of slide 21 in which preparation plate 5 can be secured in a suitable specimen holder 39. Peg 25 serves as a handle for manual operation of slide 21.

The shifter part is preferably produced from a transparent plastic that makes possible visual monitoring during the entire transfer operation of the biopsy specimen. In the embodiment shown in FIG. 5, this shifter part 26 is assembled from an upper part 27, a lower part 31, and several accessory parts. Upper part 27 is made up of two parallelepipedal shaped parts, and has a vertically extending, hollow-cylindrical orifice 28 and a horizontal slot 29. Cylinder 6 (of FIG. 1a) is inserted into orifice 28 of upper part 27 and is permanently joined to shaped part 27. Cylinder 6 has a tip 7 which corresponds in its base outline to opening 2 of a biopsy needle, and is placed asymmetrically on the underside of cylinder 6.

Upon assembly of the shifter part from the upper and lower parts, a short helical spring 36 is first placed around the portion of cylinder 6 projecting out of upper part 27. Cylinder 6 is then introduced through orifice 33 into lower part 31, and remains freely movable in said orifice.

Shaped part 27 of the upper part is then movably joined to shaped part 31 of the lower part by means of a screw 30 which is screwed into place, through a slot 29 extending horizontally through said upper part, in a horizontally extending screw thread 32 of lower part 31. Foot 34 of shaped part 31 in turn engages into groove 18 of transfer part 15, and allows the assembled shifter part 26 to be displaced in controlled fashion, as a unit, in said groove 18.

Extending on the underside of shaped part 31 which contains orifice 33 is a step 35 whose height corresponds to the diameter of a biopsy needle. This step 35 serves to clamp biopsy needle 1, which initially is laid loosely against the lateral surface of plate 20 (FIG. 3), in place between step 35 and said lateral surface of plate 20, and thereby to position it at the desired point above preparation plate 5. As an alternative to this, biopsy needle 1 can be introduced into a previously prepared cavity above preparation plate 5. A cavity of this kind can be constituted, for example, by the fact that shaped part 31 is first slid against frame 40 (inserted into opening 19) of sample holder 39, so that step 35 forms, with the lateral surface of plate 20, an accurately fitted cavity for biopsy needle 1.

Vertical displacement of parts 27 and 31 with respect to one another causes the transfer of biopsy specimen 3 from biopsy needle 1 into preparation plate 5, as was depicted in FIG. 1a.

Figure 6:
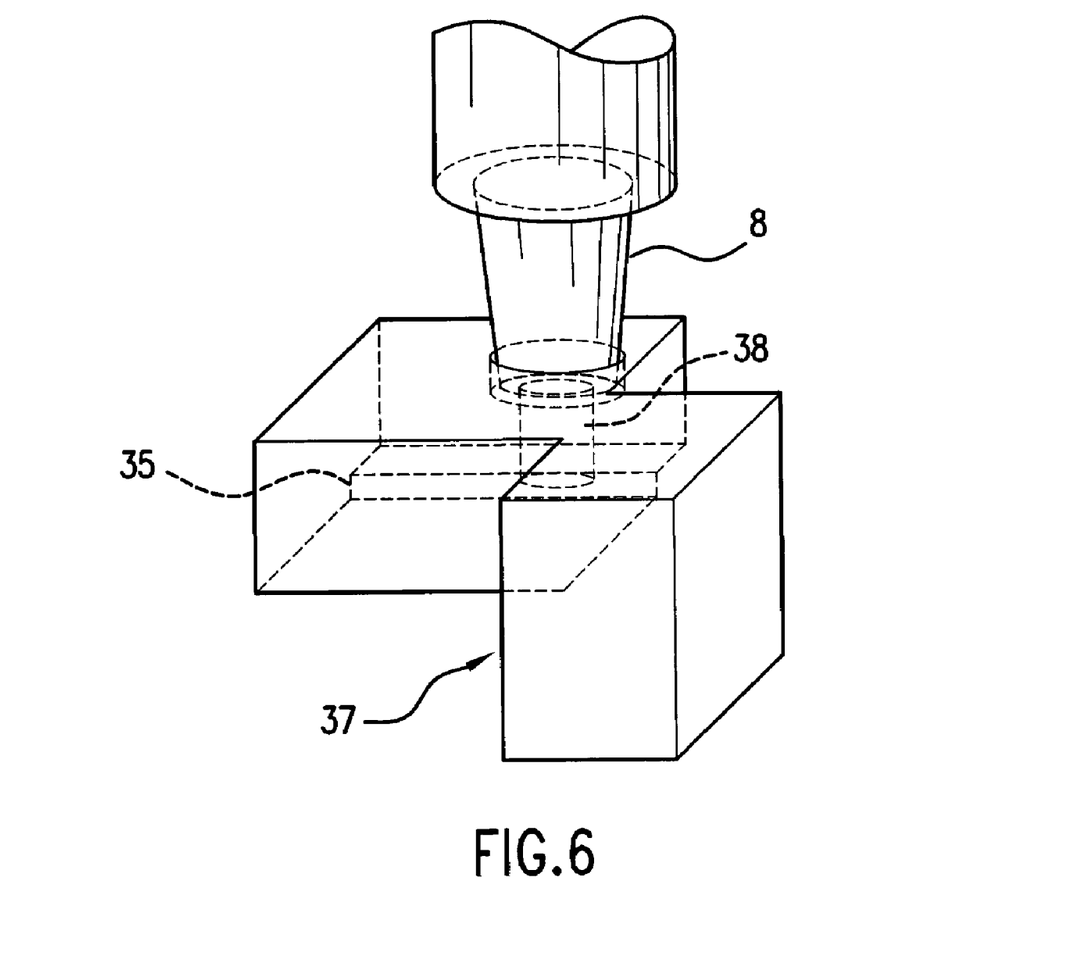

As an alternative to this embodiment assembled from multiple parts, an embodiment of a shifter part as shown in FIG. 6, made up of a single part, can be used. This serves to transfer mechanically sensitive biopsy specimens into preparation plate 5 by means of a stream of fluid, rather than by the action of a solid cylinder 6. This embodiment comprises a shaped part 37 which has a vertically extending hollow-cylindrical orifice 38. The shape of this orifice 38 corresponds to that of transition part 9 of FIG. 1b, and serves to receive injection syringe 8 during flushing of a biopsy specimen 3 out of biopsy needle 1 into a preparation plate 5. This shaped part 37 also has on its underside a step 35 which serves, together with plate 20, to clamp biopsy needle 1 in place and which, in the manner already described, contributes to the formation of a cavity into which biopsy needle 1 can subsequently be inserted.

This one-piece shifter part 37 serves for the transfer of mechanically sensitive specimens, e.g. brain tissue specimens. In this method, the excess flushing fluid leaves the apparatus through the two grooves 16 and 18.

Figure 7:
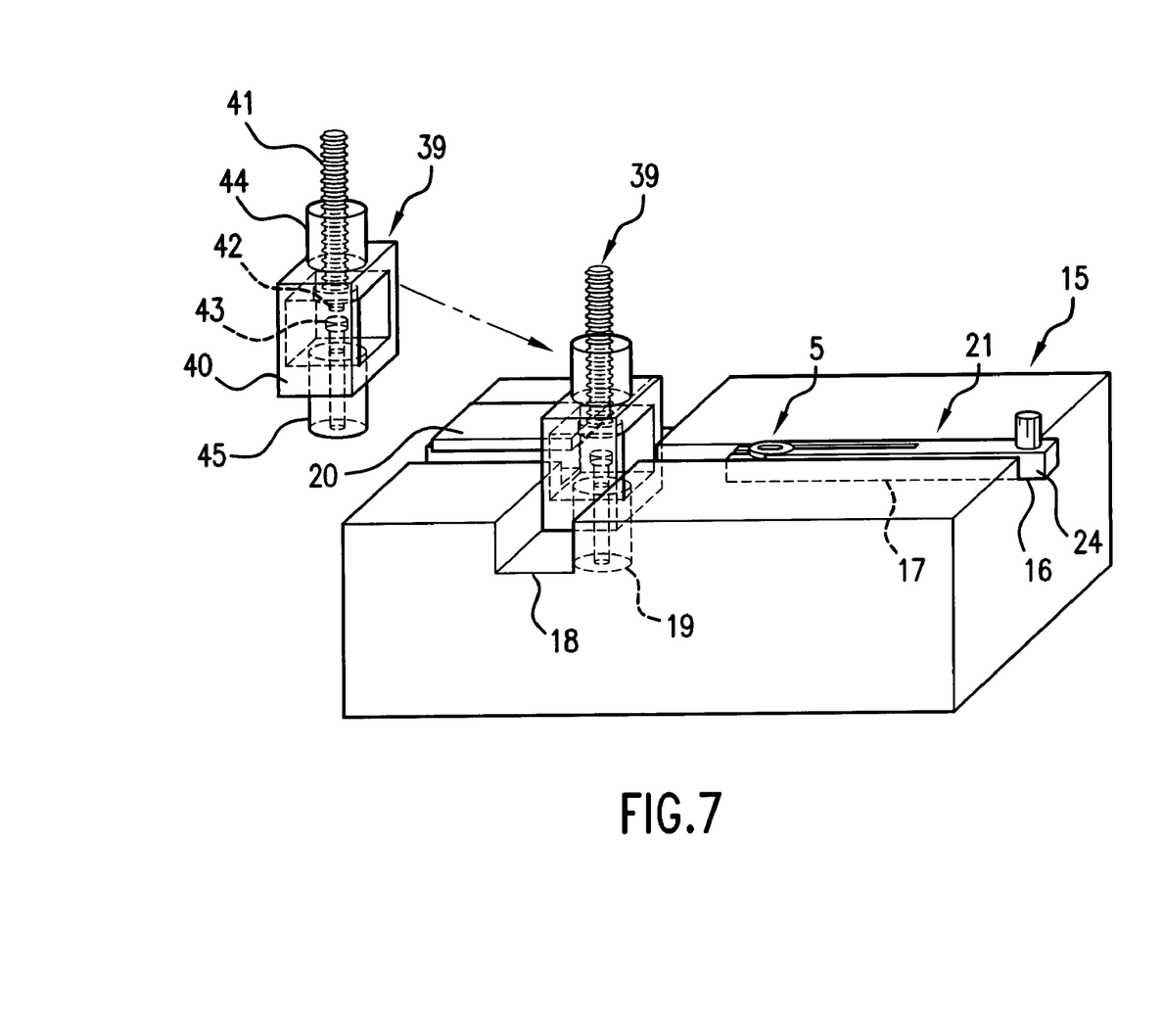
FIG. 7 shows a transfer part with an inserted slide and an empty preparation plate, as well as the inserted specimen holder in the ready position.
Figure 8:
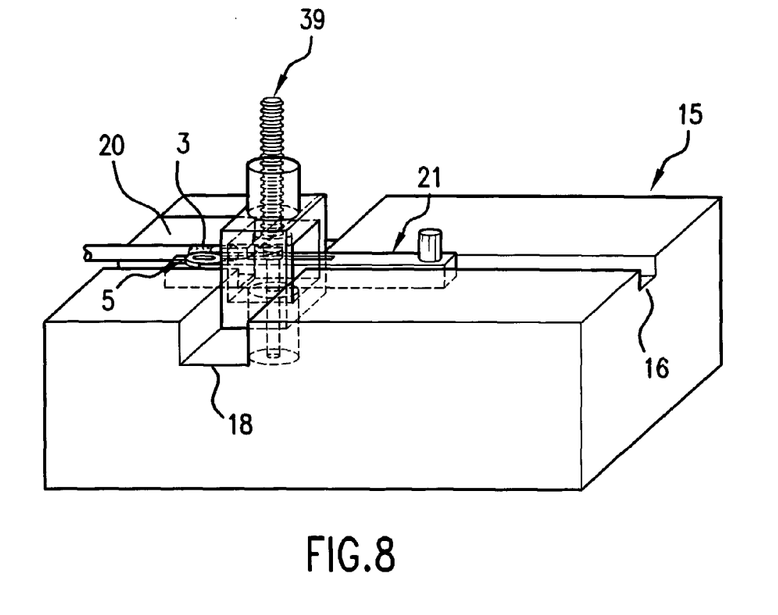
FIG. 8 shows a transfer part with a biopsy needle filled with the biopsy specimen.
Figure 9:
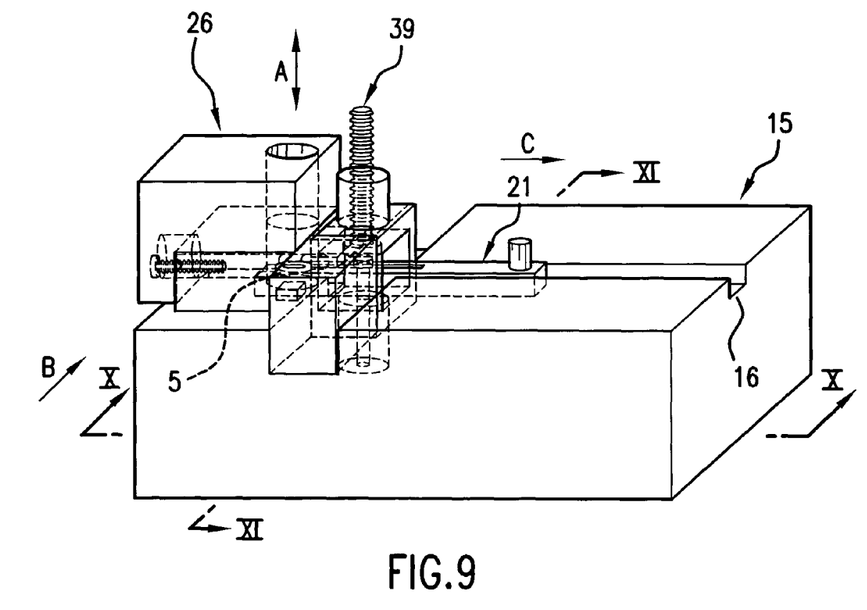
FIG. 9 shows a transfer part with a biopsy needle and shifter part placed on it, and—indicated schematically with arrows—the motions necessary in order to transfer the biopsy from the biopsy needle into the preparation plate and the specimen holder.

The method for using the apparatus according to the present invention is depicted in FIGS. 7 through 9.

In a first method step, specimen holder 39 is inserted into groove 16 and into opening 19 of transfer part 15 (FIG. 7). A product designed for a high-pressure freezing unit (Product Bulletin 16 50 02 of December 2000, of Leica Microsystems GmbH (Leica EM PACT)) serves, for example as the specimen holder. This specimen holder 39 comprises the following individual parts: A casing 40 serves as a mechanical frame for reception of the other components. Inserted in a corresponding screw thread in the longitudinal axis of said frame 40 is a screw 41 which has a diamond sealing surface 42 at its end protruding into the frame, and which serves to clamp preparation plate 5 securely in place. Provided on the side of frame 40 opposite the screw thread is a support apparatus 43 for preparation plate 5, which in turn is connected to the pressure line for transferring high pressure during the freezing operation. Extensions 44 and 45 of frame 40, configured as hollow cylinders, serve to anchor the specimen holder in the high-pressure freezing unit; extension 45 additionally immobilizes the specimen holder in accurately fitting fashion in opening 19 of transfer part 15 during transfer of the biopsy specimens.

Slide 21 with the empty preparation plate 5 is then inserted into groove 16 of transfer part 15 so that peg 24 comes to a stop against the outer edge of transfer part 15 (position I in FIG. 10*b*), and an empty preparation plate 5 is placed into recess 22. Slide 21 with the empty preparation plate 5 is then slid into said groove 16 until peg 24 comes to a stop against the end of depression 17 adjacent to groove 18 (position II in FIGS. 10*b* and 10*c*). Preparation plate 5 is now in a defined position and is ready for reception of a biopsy specimen.

The biopsy is then taken from the tissue using a commercially obtainable microbiopsy apparatus. If an opening in the lance of the biopsy needle which is smaller than in the methods previously described is used, it has been found that upon insertion of the needle into the tissue, the tip and opening of the lance are usefully immovably positioned in front of the cutting edge of the hollow needle. As a result, and in contrast to the methods previously described (Hohenberg op. cit. p. 135), the opening can be positioned very accurately in the tissue. Because of the relatively slow advance of the lance, in contrast to the commercially obtainable apparatuses the tissue can fill the opening of the lance better and more easily. In order to cut off the tissue that has entered the small opening in this fashion, the hollow needle is slid over the lance in a manner known per se. The needle is then pulled out of the tissue, and biopsy specimen 3 is exposed again by pulling the hollow needle back.

With a predetermined insertion depth along the lateral surface of plate 20, biopsy specimen 3 in opening 2 of biopsy needle 1 comes to rest exactly above specimen well 4 of a preparation plate 5, as depicted in FIG. 8. Shifter part 26 or 37 (only shifter part 26 is depicted in FIG. 9) is then introduced into groove 18 of transfer part 15 and displaced into it until step 35 on the underside of shaped part 31 presses biopsy needle 1 against the lateral surface of plate 20 and clamps it in place. As a result, opening 2 of biopsy needle 1 is positioned exactly above specimen well 4 of preparation plate 5 prepared for it.

Transfer of a biopsy specimen 3 from biopsy needle 1 into specimen plate 5 and then into specimen holder 39 is depicted in FIGS. 10*a* through 10*g* (longitudinal section through the center of groove 18).

Figure 10A:
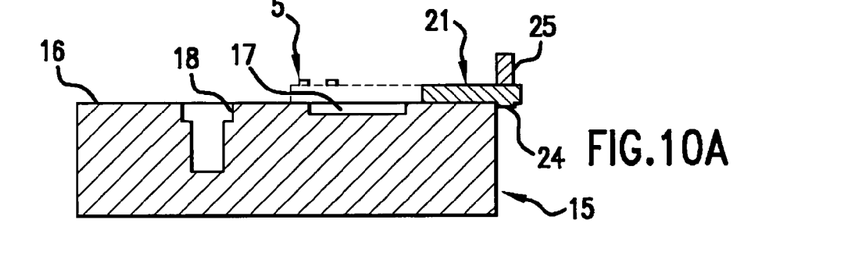
FIGS. 10a through 10g show longitudinal sections through a transfer part with the various steps of transferring a biopsy specimen.

In order to insert preparation plate 5 into slide 21, slide 21 is positioned in groove 16 at the end facing away from groove 18. Peg 24 protrudes beyond the upper edge of transfer part 15 (position I) (FIG. 10*a*).

Figure 10B:
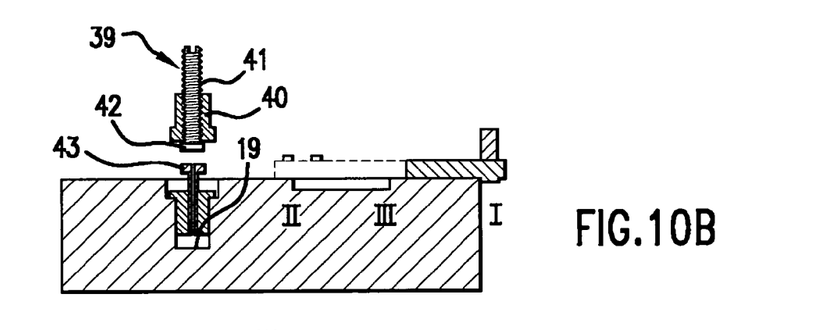

Specimen holder 39 is then inserted into groove 18 and opening 19 (FIG. 10*b*).

Figure 10C:
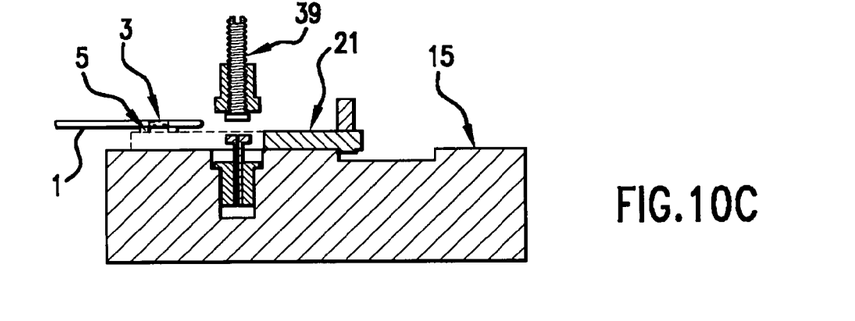

Slide 21 is displaced as far as the stop (position II) of peg 24 located closer to specimen holder 39, so that preparation plate 5 lies partially beneath plate 20 (not depicted). Biopsy needle 1 filled with a biopsy specimen 3 is then laid loosely against the lateral surface of plate 20, so that biopsy specimen 3 lies exactly above specimen well 4 of preparation plate 5. The correct position of biopsy specimen 3 in the longitudinal axis of groove 16 is defined by guiding the biopsy gun (not depicted in the Figure), in which biopsy needle 1 is mounted, as far as a predetermined stop on the apparatus, for example against the outer edge of a base plate (not depicted in the Figure) (FIG. 10*c*). As an alternative thereto, this position of biopsy needle 1 in the longitudinal axis of groove 16 can also be defined by guiding its tip as far as a predefined stop, for example in shaped part 31 or on the lateral wall of specimen holder 39.

Figure 10D:
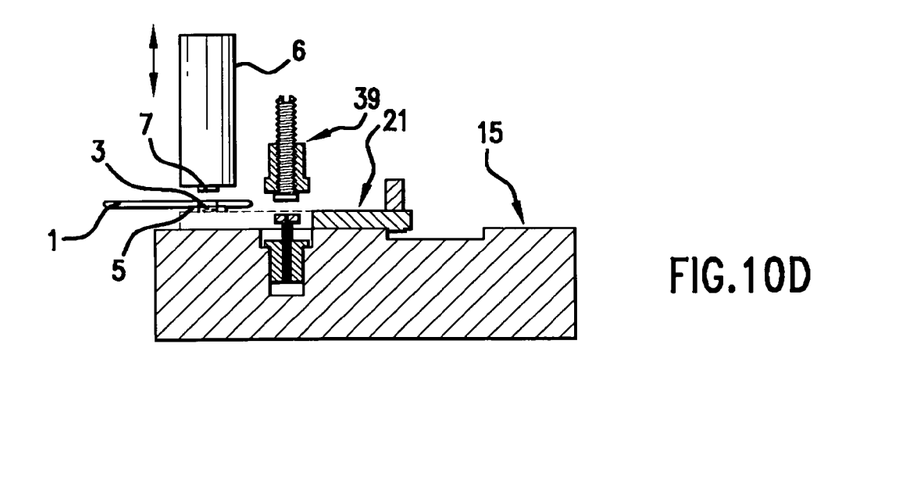

Displacement of shifter part 31 or 37 in groove 18 to the point of contact against the lateral surface of frame 40 of specimen holder 39 causes biopsy needle 1 with biopsy specimen 3 to be secured between the shifter part and the lateral surface of plate 20. As an alternative thereto, biopsy needle 1 can also be introduced into a previously prepared cavity. A cavity of this kind can be formed, for example, in such a way that the last two method steps are transposed: after the positioning of preparation plate 5 in position II, the shifter part is inserted into groove 18 and displaced until the lateral surface of shaped part 31 or 37 is resting against the lateral surface of frame 40 of specimen holder 39. Biopsy needle 1 is then introduced into the cavity thereby formed between groove 18, the lateral surface of 31 or 37, and the lateral surface of plate 20. Biopsy specimen 3 is then pushed, by a vertical motion of cylinder 6, from biopsy needle 1 into specimen plate 5 (FIG. 10*d*).

Figure 10E:
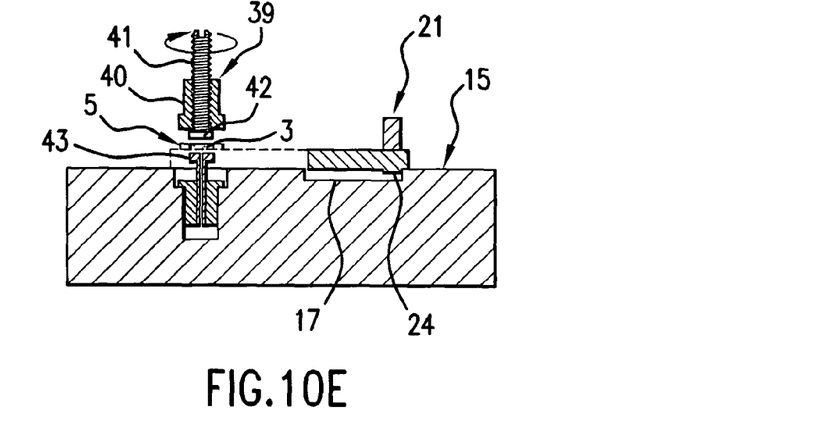

Slide 21 is next displaced to the opposite stop of peg 24 in depression 17 (position III). Preparation plate 5 filled with biopsy specimen 3 is thereby correctly positioned in specimen holder 39 and clamped in place by means of screw 41 (FIG. 10*e*).

Figure 10F:
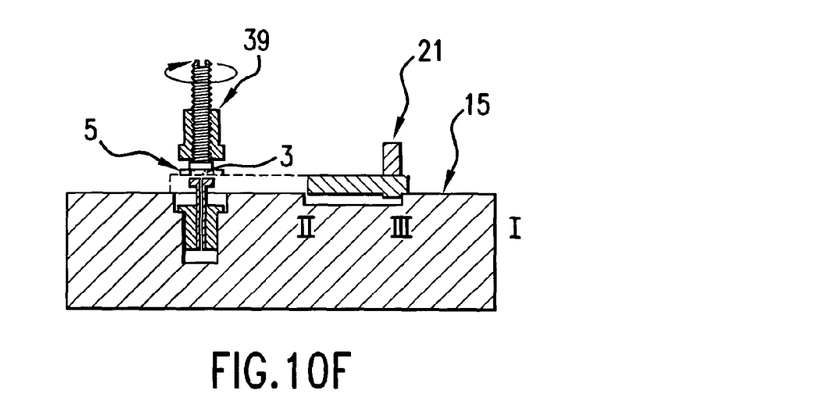
Figure 10G:
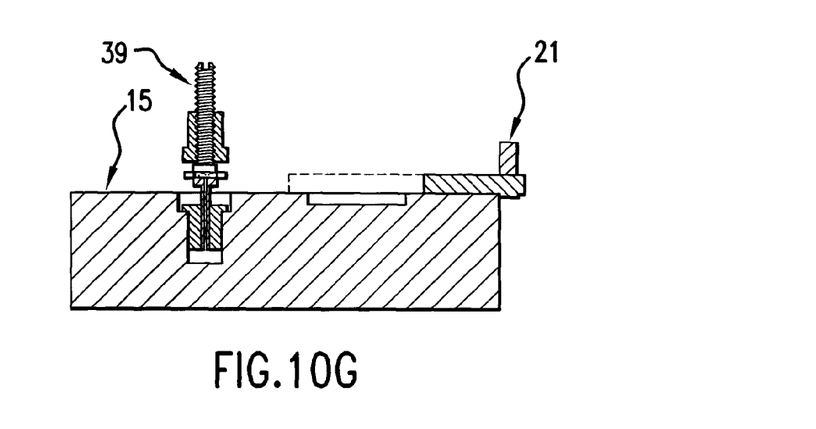

Lastly, slide 21 is pulled back into its starting position at the farther end of groove 16, and peg 24 is displaced back out of position III into its starting position I on the outer edge of transfer part 15 (FIGS. 10*f* and 10*g*). Specimen holder 39, with preparation plate 5 clamped in place, is then secured in a manipulator which allows removal from groove 18 and opening 19, and freezing of the biopsy specimen.

FIGS. 11*a* through 11*e* depict the introduction of biopsy needle 1 and the transfer of biopsy specimen 3 from biopsy needle 1 into preparation plate 5, in a cross section through a transfer part 15 and through an embodiment of a shifter part made up of the two shaped parts 27 and 31.

Figures 11A, 11B:
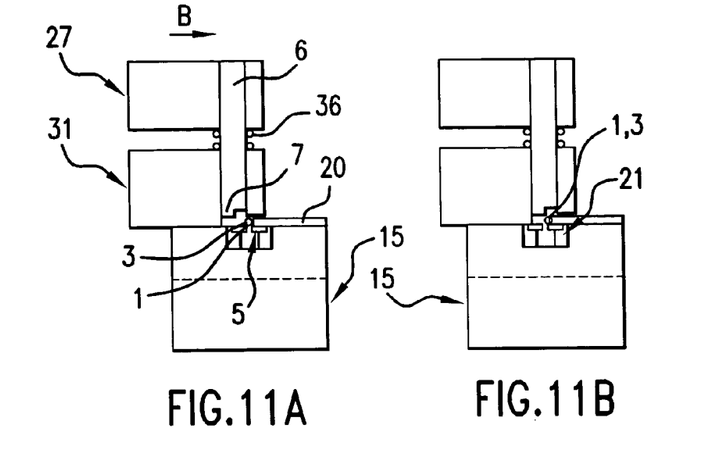
FIGS. 11a through 11e show cross sections through a transfer part with the various steps of transferring a biopsy specimen.

Biopsy needle 1 is laid in the predetermined position, perpendicular to the plane of the drawing, against the lateral surface of plate 20, which is permanently mounted on the upper side of shaped part 15 and in turn partially overlaps preparation plate 5 (FIG. 11*a*).

In order to immobilize biopsy needle 1, the shifter part made up of the two shaped parts 27 and 31 is introduced into groove 18 and is pushed farther in the direction of biopsy needle 1 until the cut-out step 35 on the underside of shaped part 31 comes to a stop against biopsy needle 1. As a result, the latter is clamped in place between step 35, the lateral surface of plate 20, and preparation plate 5, and is immobilized in that position. Tip 7 of cylinder 6 is now located vertically above opening 2, filled with biopsy specimen 3, of biopsy needle 1 (FIG. 11*b*).

As an alternative thereto, biopsy needle 1 can also be introduced into a previously prepared cavity. A cavity of this kind can be formed, for example, in such a way that the last two method steps are transposed: After the positioning of preparation plate 5 in position II, shifter part is inserted into groove 18 and displaced until the lateral surface of shaped part 31 or 37 is resting against the lateral surface of frame 40 of specimen holder 39. Biopsy needle 1 is then introduced into the cavity thereby formed between groove 18, the lateral surface of 31 or 37, and the lateral surface of plate 20.

Figure 11C:
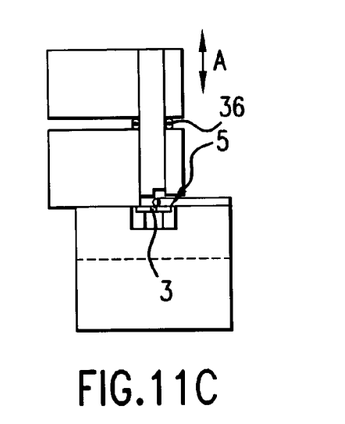

Shaped part 27, with cylinder 6, is then displaced by hand vertically downward in arrow direction A-A as depicted. As a result of this vertical motion, tip 7 of cylinder 6 pushes biopsy specimen 3 out of opening 2 of biopsy needle 1 into depression 4 of the prepared preparation plate 5. This vertical motion requires that the spring force of helical spring 36, placed between shaped parts 27 and 31, be overcome (FIG. 11c).

Figure 11D:
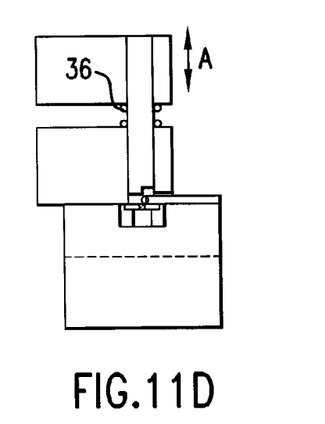

When the force exerted on shaped part 27 is then released, cylinder 6 is pushed back into its starting position by the spring force of helical spring 36. As a result, the empty biopsy needle 1 is once again movable in its longitudinal axis and can be pulled back (FIG. 11d).

Figure 11E:
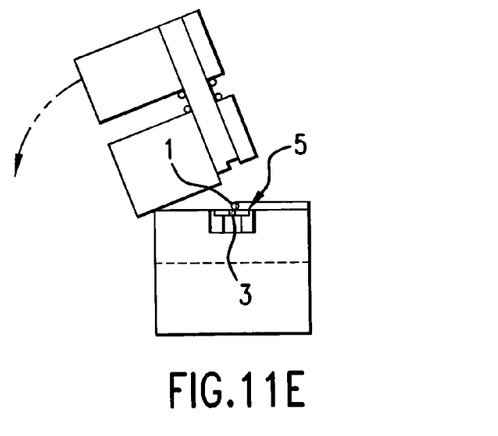

Lastly, shifter part 26 made up of the two shaped parts 27 and 31 is ideally rotated about its longitudinal axis and thereby removed from transfer part 15. The preparation plate filled with biopsy specimen 3 can now be displaced in the direction of specimen holder 39 and clamped in place therein. The underside of shaped part 31, and tip 7 of cylinder 6, are cleaned, and are available for the next specimen transfer (FIG. 11e).

What is claimed is:

1. An apparatus for handling a biopsy specimen, comprising:
   a) a transfer part;
   b) a slide, displaceable and exchangeable on the transfer part, for transporting a flat preparation plate;
   c) the flat preparation plate, exchangeable on said slide, for receiving the biopsy specimen; and
   d) a shifter part, displaceable and exchangeable on said transfer part, having at least one vertically extending channel for introduction of a biopsy transfer mechanism for transferring the biopsy specimen out of an opening of a biopsy needle into a specimen well of the preparation plate.

2. The apparatus as defined in claim 1, wherein the biopsy needle has an axially extending opening having dimensions in the range of 0.2 to 0.3 mm deep and 1.0 to 5.0 mm long.

3. The apparatus as defined in claim 1, wherein the preparation plate has a circular shape as well as at least one cavity for the reception of the biopsy specimen.

4. The apparatus as defined in claim 1, wherein a contour of the preparation plate comprises at least one corner which fits a corresponding corner of a recess of the slide, and at least one cavity for receiving the biopsy specimen.

5. The apparatus as defined in claim 1, wherein the preparation plate is produced from a metallic material.

6. The apparatus as defined in claim 1, wherein the preparation plate comprises a shaped part made of a metallic material, and a metal foil permanently joined to said shaped part.

7. The apparatus as defined in claim 1, wherein the preparation plate has a maximum diameter of 6.2 mm; a maximum thickness of 5 mm; and a slot with a maximum length of 5 mm.

8. The apparatus as defined in claim 1, wherein the displaceable and exchangeable slide comprises, for transport of the flat preparation plate, a flat strip, a recess at one end of the strip, a vertical slot extending in a longitudinal axis of the strip, a locking peg on an underside, and a handle in a form of a peg on an upper side of the strip.

9. The apparatus as defined in claim 8, wherein the recess in the strip forms a circular arc having an extension of at most 220°.

10. The apparatus as defined in claim 8, wherein the recess in the strip has corners into which corresponding corners of the preparation plate fit.

11. The apparatus as defined in claim 1, wherein the transfer part comprises at least one parallelepipedal shaped part which has on its upper side a groove extending in a longitudinal axis for reception of the slide, and a groove extending in a transverse axis of the shaped part for reception of the shifter part.

12. The apparatus as defined in claim 11, wherein the shaped part of the transfer part has, in the bottom of the groove extending in the longitudinal axis, a further depression, extending over a portion of the groove extending in the longitudinal axis, for reception of a locking peg of the slide; a vertically extending, hollow-cylindrical opening in the bottom of the groove extending in the transverse axis for reception of a specimen holder; and, on its upper side, a plate, permanently joined to the shaped part, which overlaps a portion of the groove extending in the longitudinal axis and serves to guide the biopsy needle prior to transfer of the biopsy specimen.

13. The apparatus as defined in claim 12, wherein the plate and the preparation plate lying on the slide form, with theone vertical lateral wall of the groove extending in the longitudinal axis, a cavity extending in the horizontal direction for immobilization of the biopsy needle filled with the biopsy specimen.

14. The apparatus as defined in claim 1, wherein the shifter part comprises:
   a) a first shaped part as an upper part;
   b) a second shaped part as a lower part;
   c) a cylinder, permanently inserted in a vertically extending orifice of the upper part and displaceably and exehangeably inserted in a vertically extending orifice of the lower part;
   d) a short helical spring placed around the cylinder and arranged between the upper and lower parts; and
   e) a slot extending horizontally in the upper part, with which the upper part is anchored to the lower part with a screw connection in such a way that the upper part and lower part are displaceable with respect to one another in a longitudinal axis of the cylinder by overcoming a spring force of the helical spring.

15. The apparatus as defined in claim 1, wherein the shifter part comprises a shaped part which comprises a substantially hollow-cylindrical orifice, extending vertically through the entire shaped part, for reception of a front part of an injection syringe; and, on an sunderside of the shaped part, a cut-out step extending substantially in a longitudinal axis of the shaped part.

16. A method for using an apparatus for handling a biopsy specimen comprising: a transfer part; a displaceable and exchangeable slide on the transfer part for transporting a flat preparation plate; and a displaceable and exchangeable shifter part on said transfer part, having at least one vertically extending channel for introduction of a biopsy transfer mechanism for transferring the biopsy specimen out of an opening of a biopsy needle into a specimen well of the preparation plate comprising:
   a) an empty preparation plate is inserted into the slide into a first position;
   b) a specimen holder is inserted into an opening of the transfer part;

c) said slide is displaced into a second position in a groove of the transfer part as far as a centrally arranged stop of a depression in the transfer part;
d) the shifter part is inserted into the groove of the transfer part;
e) the biopsy needle with the biopsy specimen is immobilized vertically above the specimen well of the preparation plate;
f) the biopsy specimen is introduced into the specimen well of the preparation plate;
g) the shifter part is removed again from the groove of the transfer part;
h) the slide, with the preparation plate filled with the biopsy specimen, is displaced into a third position in the groove of the transfer part against a non-central stop in the depression; and
i) the preparation plate is secured in the specimen holder, located in the opening of the transfer part, by screw movements.

17. The method as defined in claim 16, wherein the step of immobilizing the biopsy needle with the biopsy specimen vertically above the specimen well of the preparation plate comprises the steps of loosely placing the biopsy needle against a lateral wall of a plate mounted on an upper side of the transfer part and clamping the biopsy needle in place, by displacement of the transfer part in the groove, between the preparation plate, the lateral wall of the plate mounted on the upper side of the transfer part, and a step on an underside of the transfer part.

18. The method as defined in claim 16, wherein the step of immobilizing the biopsy needle with the biopsy specimen vertically above the specimen well of a preparation plate comprises the step of introducing the biopsy needle.

19. The method as defined in claim 18, wherein the previously prepared cavity is formed by the preparation plate, a lateral wall of a plate mounted on an upper side of the transfer part, and a step on an underside of the transfer part.

20. The method as defined in claim 16, wherein the biopsy specimen is transferred downward, by a vertical motion of a cylinder of the transfer part, into the specimen well of the preparation plate.

21. The method as defined in claim 16, wherein the biopsy specimen is conveyed through a vertical channel of the shifter part, by a stream of fluid, into the specimen well of a preparation plate, wherein excess flushing fluid emerges from the transfer part through the groove of the transfer part.

* * * * *